(12) United States Patent
Mann et al.

(10) Patent No.: US 9,877,481 B2
(45) Date of Patent: Jan. 30, 2018

(54) SYNERGISTIC WEED CONTROL FROM APPLICATIONS OF PENOXSULAM AND BENZOBICYCLON OR CLOMAZONE AND BENZOBICYCLON

(71) Applicant: Dow AgroSciences LLC, Indianapolis, IN (US)

(72) Inventors: Richard K. Mann, Franklin, IN (US); Carla N. Yerkes, Crawfordsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/202,416

(22) Filed: Mar. 10, 2014

(65) Prior Publication Data

US 2014/0274710 A1    Sep. 18, 2014

Related U.S. Application Data

(60) Provisional application No. 61/788,672, filed on Mar. 15, 2013.

(51) Int. Cl.
*A01N 41/10* (2006.01)
*A01N 43/90* (2006.01)

(52) U.S. Cl.
CPC ............. *A01N 41/10* (2013.01); *A01N 43/90* (2013.01)

(58) Field of Classification Search
CPC ................................ A01N 41/10; A01N 43/90
See application file for complete search history.

(56) References Cited

U.S. PATENT DOCUMENTS

| | | | |
|---|---|---|---|
| 5,858,924 | A | 1/1999 | Ehret Al |
| 7,314,849 | B2 | 1/2008 | Balko et al. |
| 7,432,227 | B2 | 10/2008 | Balko et al. |
| 7,786,044 | B2 | 8/2010 | Epp et al. |
| 2002/0055435 | A1 | 5/2002 | Baltruschat et al. |
| 2008/0153704 | A1 | 6/2008 | Yamaji et al. |
| 2009/0011936 | A1 | 1/2009 | Hawkes et al. |
| 2010/0099564 | A1 | 4/2010 | Hacker et al. |
| 2010/0279864 | A1 | 11/2010 | Mann et al. |

FOREIGN PATENT DOCUMENTS

| | | |
|---|---|---|
| EP | 1313369 | 6/2005 |
| KR | 20090130583 A * | 12/2009 |

OTHER PUBLICATIONS

Park, T.S., Effective Weed Control in Direct Seeded Rice on Puddled Paddy Surface on Southern Region Abstract [online]. Food and Agriculture Organization of the United Nations, Mar. 2012 [retrieved on May 1, 2015]. Retrieved from the Internet:<http://agris.fao.org/agris-search/search.do?recordID=KR2013001980> 1 page.*
Lee, I., Control of Herbicide Resistant Echinochloa Oryzoides with Pre and Post Emergent Herbicides Based on the Leaf Stages, Sep. 2011, 23rd Asian-Pacific Weed Science Society Conference, vol. 1, pp. 263-269.*
Anonymous, 2-(2,2-difluoroethoxy)-6-trifluoromethyl-1-(5,8-dimethoxy[1,2,4]triazolo[1,5-c]pyrimidin-2-yl)benzensulfonamide and its Use as a Herbicide in Mixtures, 2002, Research Disclosure, Research Disclosure No. 462055, 5 pages.*
Oh, S.W., Effects of Benzobicyclon and Penoxsulam SC Depends on a Species, Treatment Time and Water Depth in the Wet Direct-Seeded Rice, 2007, Central Research Institute of Kyung Nong Corporation, pp. 65-66, [retrieved on May 16, 2016]; Retrieved from the Internet:< http://210.101.116.28/W_files/kiss3/07401923_pv.pdf> pp. 65-66.*
International Search Report and Written Opinion, dated Jun. 18, 2014, in corresponding International Application No. PCT/US14/22450, 9 pages.
Farm Chemical International, Crop Protection Database, "Benzobicyclon," available at http://www.farmchemicalsinternational.com/crop-protection-database/#/product/detail/66700/ (accessed on May 27, 2014).
Farm Chemical International, Crop Protection Database, "Clomazone," available at http://www.farmchemicalsinternational.com/crop-protection-database/#/product/detail/100720/ (accessed on May 27, 2014).
Farm Chemical International, Crop Protection Database, "Penoxsulam," available at http://www.farmchemicalsinternational.com/crop-protection-database/#/product/detail/424174/ (accessed on May 27, 2014).
Park, T.S. et al. "Agronomic Characteristics and Herbicidal Response of Barnyard Millet Strains Under Paddy Rice." Korean Journal of Weed Science, 2012, 32: 256-262.
Tomlin, C. D. S., Ed., The Pesticide Manual: A World Compendium, "Benzobicyclon," 15th ed., BCPC: Alton, 2009, p. 96.
Tomlin, C. D. S., Ed., The Pesticide Manual: A World Compendium, "Clomazone," 15th ed., BCPC: Alton, 2009, pp. 220-222.

(Continued)

*Primary Examiner* — John Pak
*Assistant Examiner* — Andriae M Holt
(74) *Attorney, Agent, or Firm* — Michael R. Asam; Meunier Carlin & Curfman, LLC

(57) ABSTRACT

Disclosed herein are herbicidal compositions comprising a synergistic herbicidally effective amount of (a) penoxsulam or an agriculturally acceptable salt thereof, or clomazone or an agriculturally acceptable salt thereof, and (b) benzobicyclon or an agriculturally acceptable salt thereof. Also disclosed herein are methods of controlling undesirable vegetation in rice, which comprise applying to vegetation or an area adjacent the vegetation or applying to soil or water to prevent the emergence or growth of vegetation (a) penoxsulam or an agriculturally acceptable salt thereof, or clomazone or an agriculturally acceptable salt thereof, and (b) benzobicyclon or an agriculturally acceptable salt thereof, wherein (a) and (b) are each added in an amount sufficient to produce a synergistic herbicidal effect.

13 Claims, No Drawings

(56) References Cited

OTHER PUBLICATIONS

Tomlin, C. D. S., Ed., The Pesticide Manual: A World Compendium, "Penoxsulam," 15th ed., BCPC: Alton, 2009, pp. 874-875.
Extended EP Search Report issued in Application No. 14767530.0, dated Sep. 28, 2016.
Eckert, et al., "Comprehensive rice research", Annual Report, Jan. 1, 2012-Dec. 31, 2012, 48 pages.

* cited by examiner

US 9,877,481 B2

SYNERGISTIC WEED CONTROL FROM APPLICATIONS OF PENOXSULAM AND BENZOBICYCLON OR CLOMAZONE AND BENZOBICYCLON

CROSS REFERENCE TO RELATED APPLICATIONS

This application claims the benefit of U.S. Provisional Patent Application Ser. No. 61/788,672 filed Mar. 15, 2013, the disclosure of which is expressly incorporated herein by reference.

FIELD OF THE DISCLOSURE

The present disclosure relates to herbicidal compositions comprising a synergistic herbicidally effective amount of (a) penoxsulam or an agriculturally acceptable salt thereof, or clomazone or an agriculturally acceptable salt thereof, and (b) benzobicyclon or an agriculturally acceptable salt thereof. The present disclosure also relates to methods for controlling undesirable vegetation in rice.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) penoxsulam or an agriculturally acceptable salt thereof, or clomazone or an agriculturally acceptable salt thereof, and (b) benzobicyclon or an agriculturally acceptable salt thereof, display a synergistic herbicidal effect when applied in combination.

Accordingly, the present disclosure relates to herbicidal compositions comprising a synergistic herbicidally effective amount of (a) penoxsulam or an agriculturally acceptable salt thereof, or clomazone or an agriculturally acceptable salt thereof, and (b) benzobicyclon or an agriculturally acceptable salt thereof. In some embodiments, (a) includes penoxsulam or an agriculturally acceptable salt thereof. In these cases, the weight ratio of (a) to (b) can be from 1:80 to 50:1 (e.g., from 1:30 to 1.6:1 or from 1:10 to 1:2.5). In some embodiments, (a) includes clomazone or an agriculturally acceptable salt thereof. In these cases, the weight ratio of (a) to (b) can be from 1:4 to 50:1 (e.g., from 1:3 to 28:1 or 1.12:1 to 2.24:1).

In some embodiments, the composition further comprises an additional pesticide (e.g., benzofenap, cyhalofop, daimuron, pentoxazone, esprocarb, pyrazosulfuron, butachlor, pretilachlor, metazosulfuron, bensulfuronmethyl, imazosulfuron, azimsulfuron, bromobutide, benfuresate, mesotrione, oxazichlomefone, and agriculturally acceptable salts or esters thereof, or combinations thereof). In some embodiments, the composition further comprises a herbicidal safener, an agriculturally acceptable adjuvant or carrier, or a combination thereof. In certain embodiments, the composition is provided as a herbicidal concentrate.

The present disclosure also relates to methods of controlling undesirable vegetation in rice, which comprise applying to vegetation or an area adjacent the vegetation or applying to soil or water to prevent the emergence or growth of vegetation (a) penoxsulam or an agriculturally acceptable salt thereof, or clomazone or an agriculturally acceptable salt thereof, and (b) benzobicyclon or an agriculturally acceptable salt thereof, wherein (a) and (b) are each applied in an amount sufficient to produce a synergistic herbicidal effect. In some embodiments, (a) and (b) are applied simultaneously.

The undesirable vegetation can be, for example, a broadleaf weed, a sedge weed, a grassy weed, or combinations thereof. In some embodiments, the undesirable vegetation includes purple nutsedge or early watergrass. In certain embodiments, the undesirable vegetation is controlled in rice that is resistant to, for instance, herbicides, pathogens, and/or insects.

In some embodiments, (a) includes penoxsulam or an agriculturally acceptable salt thereof. In some of these embodiments, (a) can be applied in an amount of from 5-50 grams of active ingredient per hectare (g ai/ha). In some embodiments, (b) is applied in an amount of from 20-400 g ai/ha. Penoxsulam (a) and benzobicyclon (b) can be applied in a weight ratio of from 1:80 to 2.5:1 (e.g., 1:30 to 1.6:1, from 1:15 to 1:1, or from 1:10 to 1:2.5).

In some embodiments, (a) includes clomazone or an agriculturally acceptable salt thereof. In some of these embodiments, (a) can be applied in an amount of from 100-1000 g ai/ha. In some embodiments, (b) is applied in an amount of from 20-400 g ai/ha. Clomazone (a) and benzobicyclon (b) can be applied in a weight ratio of from 1:4 to 50:1 (e.g., from 1:3 to 28:1, from 1:2 to 10:1, or from 1.12:1 to 2.24:1).

The description below sets forth details of one or more embodiments of the present disclosure. Other features, objects, and advantages will be apparent from the description and from the claims.

DETAILED DESCRIPTION

The present disclosure relates to herbicidal compositions comprising a synergistic herbicidally effective amount of (a) penoxsulam or an agriculturally acceptable salt thereof, or clomazone or an agriculturally acceptable salt thereof, and (b) benzobicyclon or an agriculturally acceptable salt thereof. The present disclosure also relates to methods for controlling undesirable vegetation in rice.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Penoxsulam

Compositions and methods of the present disclosure can include penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Loughner, et al.

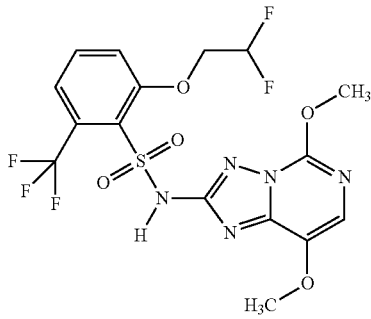 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, olamine salts, and diglycolamine salts.

Penoxsulam can be used, for example, to control grass, broadleaf and sedge weeds in rice, to control broadleaf weeds in cereal, tree and vine and sorghum crops, and to control grass, broadleaf, and sedge weeds in lawns (e.g., residential, industrial, and institutional), golf courses, parks, cemeteries, athletic fields, sod farms, range and pasture, rights-of-way, roadsides, and other crop and non-crop uses. Its herbicidal activity is described in Tomlin, C. D. S., Ed. *The Pesticide Manual: A World Compendium*, 15$^{th}$ ed.; BCPC: Alton, 2009 (hereafter "The Pesticide Manual, Fifteenth Edition, 2009"). Penoxsulam is or has been commercially available, for example, from Dow AgroSciences, LLC under the trademarks CLIPPER®, BENGALA®, FENCER®, WIDEATTACK®, SAPPHIRE®, VIPER®, GRASP®, and GRANITE®, and from SePRO Corporation under the trademark GALLEON®.

Penoxsulam or an agriculturally acceptable salt thereof can be applied to vegetation or an area adjacent the vegetation or applied to soil or water to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil or water to prevent the emergence or growth of vegetation in an amount of 5 grams of active ingredient per hectare (g ai/ha) or greater (e.g., 10 g ai/ha or greater, 15 g ai/ha or greater, 20 g ai/ha or greater, 25 g ai/ha or greater, 30 g ai/ha or greater, 35 g ai/ha or greater, 40 g ai/ha or greater, or 45 g ai/ha or greater). In some embodiments, the penoxsulam or agriculturally acceptable salt thereof is applied to vegetation or an area adjacent the vegetation or applied to soil or water to prevent the emergence or growth of vegetation in an amount of 50 g ai/ha or less (e.g., 45 g ai/ha or less, 40 g ai/ha or less, 35 g ai/ha or less, 30 g ai/ha or less, 25 g ai/ha or less, 20 g ai/ha or less, 15 g ai/ha or less, or 10 g ai/ha or less).

Penoxsulam can be applied to vegetation or an area adjacent the vegetation or applied to soil or water to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil or water to prevent the emergence or growth of vegetation in an amount of from 5-50 g ai/ha (e.g., from 6-45 g ai/ha, from 7-40 g ai/ha, from 8-35 g ai/ha, from 9-30 g ai/ha, from 10-25 g ai/ha, or from 11-20 g ai/ha).

Clomazone

Compositions and methods of the present disclosure can include clomazone or an agriculturally acceptable salt thereof. Clomazone (i.e., 2-[(2-chlorophenyl)methyl]-4,4-dimethyl-3-isoxazolidinone, also referred to as dimethazone), shown below, is an isoxazolidinone herbicide that can be used to control grassy weeds in rice. Clomazone can also be used to control undesirable vegetation in beans, cabbage, cotton, cucumbers, melons, peas, peppers, rice, soybeans, squash, sugarcane, sweet potato, tobacco, tuberous and corm vegetables, and in chemical fallow wheat fields. Its herbicidal activity is described in *The Pesticide Manual*, Fifteenth Edition, 2009.

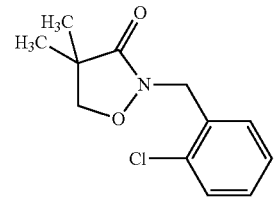 [SMILES: CC1(C)CON(Cc2ccccc2Cl)C1=O]

In some embodiments, clomazone can be provided as an agriculturally acceptable salt of clomazone. Exemplary agriculturally acceptable salts of clomazone include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri (hydroxyethyl)ammonium, hydroxypropylammonium, di(hydroxypropyl)ammonium and tri(hydroxypropyl)ammonium salts, olamine salts, and diglycolamine salts.

Clomazone is or has been commercially available, for example, under the trademarks COMMAND® (by FMC Corp.), REACTOR® (by Cheminova A/S), FERTICLO® (by Fertiagro Pte. Ltd.), KALIF® (by Makhteshim Agan Group), PILARMAND® (by Pilar AgriScience (Canada) Corp.), RAPTOR® (by Insecticidas Internacionales), JAQUE® (by Proficol), MARK-IT® (by Sharp Formulators Co., Ltd.), WOPRO-CLOMAZONE® (by B.V. Industrie- & Handelsonderneming Simonis), and CERANO® (by Wilbur-Ellis Co.).

The clomazone or an agriculturally acceptable salt thereof can be used in an amount sufficient to induce a herbicidal effect. In some embodiments, the clomazone or agriculturally acceptable salt thereof is applied to vegetation or an area adjacent the vegetation or applied to soil or water to prevent the emergence or growth of vegetation in an amount of 100 grams of active ingredient per hectare (g ai/ha) or greater (e.g., 125 g ai/ha or greater, 150 g ai/ha or greater, 200 g ai/ha or greater, 250 g ai/ha or greater, 300 g ai/ha or greater, 350 g ai/ha or greater, 400 g ai/ha or greater, 450 g ai/ha or greater, 500 g ai/ha or greater, 550 g ai/ha or greater, 600 g ai/ha or greater, 650 g ai/ha or greater, 700 g ai/ha or greater, 750 g ai/ha or greater, 800 g ai/ha or greater, 850 g ai/ha or greater, 900 g ai/ha or greater, or 950 g ai/ha or greater). In some embodiments, the clomazone or agriculturally acceptable salt thereof is applied to vegetation or an area adjacent the vegetation or applied to soil or water to prevent the emergence or growth of vegetation in an amount of 1000 g ai/ha or less (e.g., 950 g ai/ha or less, 900 g ai/ha or less, 850 g ai/ha or less, 800 g ai/ha or less, 750 g ai/ha or less, 700 g ai/ha or less, 650 g ai/ha or less, 600 g ai/ha or less, 550 g ai/ha or less, 500 g ai/ha or less, 450 g ai/ha or less, 400 g ai/ha or less, 350 g ai/ha or less, 300 g ai/ha or less, 250 g ai/ha or less, 200 g ai/ha or less, 150 g ai/ha or less, 125 g ai/ha or less, or 105 g ai/ha or less)

Clomazone can be applied to vegetation or an area adjacent the vegetation or applied to soil or water to prevent the emergence or growth of vegetation in an amount ranging from any of the minimum values described above to any of the maximum values described above. In some embodiments, the clomazone or agriculturally acceptable salt thereof is applied to vegetation or an area adjacent the vegetation or applied to soil or water to prevent the emergence or growth of vegetation in an amount of from 100-1000 g ai/ha (e.g., from 200-900 g ai/ha, from 300-800 g ai/ha, from 400-700 g ai/ha, from 440-680 g ai/ha, from 500-650 g ai/ha, or from 525-625 g ai/ha).

Benzobicyclon

Compositions and methods of the present disclosure can include benzobicyclon or an agriculturally acceptable salt thereof. Benzobicyclon (i.e., 3-(2-chloro-4-mesylbenzoyl)-2-phenylthiobicyclo[3.2.1]oct-2-en-4-one), shown below, is a 4-hydroxyphenyl-pyruvate-dioxygenase (4-HPPD) inhibitor than can be used to control annual and perennial paddy weeds in direct-seeded or transplanted rice. Its herbicidal activity is described in *The Pesticide Manual*, Fifteenth Edition, 2009. Benzobicyclon is or has been commercially available, for example, from SDS Biotech K.K. (Tokyo, Japan).

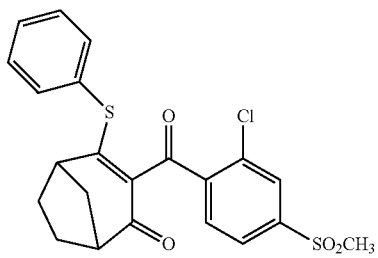 [SMILES: CS(=O)(=O)c1ccc(C(=O)C2=C(Sc3ccccc3)C3CCC(C3)C2=O)c(Cl)c1]

In some embodiments, benzobicyclon can be provided as an agriculturally acceptable salt of benzobicyclon. Exemplary agriculturally acceptable salts of benzobicyclon include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

The benzobicyclon or an agriculturally acceptable salt thereof can be used in an amount sufficient to induce a herbicidal effect. In some embodiments, the benzobicyclon or agriculturally acceptable salt thereof is applied to vegetation or an area adjacent the vegetation or applied to soil or water to prevent the emergence or growth of vegetation in an amount of 20 grams of active ingredient per hectare (g ai/ha) or greater (e.g., 25 g ai/ha or greater, 50 g ai/ha or greater, 75 g ai/ha or greater, 100 g ai/ha or greater, 125 g ai/ha or greater, 150 g ai/ha or greater, 175 g ai/ha or greater, 200 g ai/ha or greater, 225 g ai/ha or greater, 250 g ai/ha or greater, 275 g ai/ha or greater, 300 g ai/ha or greater, 325 g ai/ha or greater, 350 g ai/ha or greater, or 375 g ai/ha or greater). In some embodiments, the benzobicyclon or agriculturally acceptable salt thereof is applied to vegetation or an area adjacent the vegetation or applied to soil or water to prevent the emergence or growth of vegetation in an amount of 400 g ai/ha or less (e.g., 375 g ai/ha or less, 350 g ai/ha or less, 325 g ai/ha or less, 300 g ai/ha or less, 275 g ai/ha or less, 250 g ai/ha or less, 225 g ai/ha or less, 200 g ai/ha or less, 175 g ai/ha or less, 150 g ai/ha or less, 125 g ai/ha or less, 100 g ai/ha or less, 75 g ai/ha or less, 50 g ai/ha or less, or 25 g ai/ha or less).

Benzobicyclon can be applied to vegetation or an area adjacent the vegetation or applied to soil or water to prevent the emergence or growth of vegetation in an amount ranging from any of the minimum values described above to any of the maximum values described above. In some embodiments, the benzobicyclon or agriculturally acceptable salt thereof is applied to vegetation or an area adjacent the vegetation or applied to soil or water to prevent the emergence or growth of vegetation in an amount of from 20-400 g ai/ha (e.g., from 100-350 g ai/ha, or from 200-300 g ai/ha).

Herbicidal Mixtures or Combinations

The (a) penoxsulam or an agriculturally acceptable salt thereof, or clomazone or an agriculturally acceptable salt thereof is mixed with or applied in combination with (b) benzobicyclon or an agriculturally acceptable salt thereof in an amount sufficient to induce a synergistic herbicidal effect.

In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and*

*Antagonistic Responses of Herbicide Combinations*, WEEDS 1967, 15, 22

$$E = X + Y - \frac{X * Y}{100}$$

wherein

X=effect in percent (%) using (a) penoxsulam or an agriculturally acceptable salt thereof, or clomazone or an agriculturally acceptable salt thereof at an application rate a;

Y=effect in percent (%) using (b) benzobicyclon or an agriculturally acceptable salt thereof at an application rate b;

E=expected effect (in %) of (a)+(b) at application rates a and b.

In Colby's equation, the value E corresponds to the effect (plant control or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of (a) penoxsulam or an agriculturally acceptable salt thereof, or clomazone or an agriculturally acceptable salt thereof, and (b) benzobicyclon or an agriculturally acceptable salt thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

Provided are compositions and formulations that comprise a weight ratio of (a) penoxsulam or agriculturally acceptable salt thereof to (b) benzobicyclon or an agriculturally acceptable salt thereof that is sufficient to induce a synergistic herbicidal effect. In some embodiments, the composition or formulation can comprise (a) and (b) in a weight ratio of at least 1:80 (e.g., at least 1:70, at least 1:60, at least 1:50, at least 1:40, at least 1:30, at least 1:20, at least 1:19, at least 1:18, at least 1:17.5, at least 1:17, at least 1:16, at least 1:15, at least 1:14, at least 1:13, at least 1:12.5, at least 1:12, at least 1:11, at least 1:10, at least 1:9, at least 1:8, at least 1:7.5, at least 1:7, at least 1:6, at least 1:5, at least 1:4, at least 1:3, at least 1:2.5, at least 1:2, at least 1:1.75, at least 1:1.5, at least 1:1, at least 2:1, at least 5:1, at least 10:1, at least 15:1, at least 20:1, at least 25:1, at least 30:1, at least 35:1, at least 40:1, or at least 45:1). In some embodiments, the composition or formulation comprises (a) and (b) in a weight ratio that is less than 50:1 (e.g., less than 45:1, less than 40:1, less than 35:1, less than 30:1, less than 25:1, less than 20:1, less than 15:1, less than 10:1, less than 5:1, less than 2:1, less than 1:1, less than 1:1.25, less than 1:1.5, less than 1:1.75, less than 1:2, less than 1:2.5, less than 1:3, less than 1:4, less than 1:5, less than 1:6, less than 1:7, less than 1:7.5, less than 1:8, less than 1:9, less than 1:10, less than 1:11, less than 1:12, less than 1:12.5, less than 1:13, less than 1:14, less than 1:15, less than 1:16, less than 1:17, less than 1:17.5, less than 1:18, less than 1:19, less than 1:20, less than 1:30, less than 1:40, less than 1:45, less than 1:50, less than 1:60, or less than 1:70).

Compositions and formulations can comprise a weight ratio of (a) penoxsulam or agriculturally acceptable salt thereof to (b) benzobicyclon or an agriculturally acceptable salt thereof from any of the minimum ratios described above to any of the maximum values described above. In some embodiments, the composition or formulation comprises a weight ratio of (a) penoxsulam or agriculturally acceptable salt thereof to (b) benzobicyclon or an agriculturally acceptable salt thereof that is sufficient to induce a synergistic herbicidal effect and ranges from 1:80 to 2.5:1 (e.g., from 1:30 to 1.6:1, from 1:15 to 1:1.5, or from 1:10 to 1:2.5).

Also provided are compositions and formulations that comprise a weight ratio of (a) clomazone or agriculturally acceptable salt thereof to (b) benzobicyclon or an agriculturally acceptable salt thereof that is sufficient to induce a synergistic herbicidal effect. In some embodiments, the composition or formulation can comprise (a) and (b) in a weight ratio of at least 1:4 (e.g., at least 1:3.5, at least 1:3, at least 1:2.5, at least 1:2.25, at least 1:2, at least 1:1.9, at least 1:1.8, at least 1:1.75, at least 1:1.7, at least 1:1.6, at least 1:1.5, at least 1:1.4, at least 1:1.3, at least 1:1.25, at least 1:1.2, at least 1:1.1, at least 1:1, at least 1.1:1, at least 1.2:1, at least 1.25:1, at least 1.3:1, at least 1.4:1, at least 1.5:1, at least 1.6:1, at least 1.7:1, at least 1.75:1, at least 1.8:1, at least 1.9:1, at least 2:1, at least 2.1:1, at least 2.2:1, at least 2.3:1, at least 2.4:1, at least 2.5:1, at least 2.75:1, at least 3:1, at least 3.25:1, at least 3.5:1, at least 3.75:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, or at least 45:1). In some embodiments, the composition or formulation comprises (a) and (b) in a weight ratio that is less than 50:1 (e.g., less than 45:1, less than 40:1, less than 30:1, less than 25:1, less than 20:1, less than 15:1, less than 12.5:1, less than 10:1, less than 7.5:1, less than 5:1, less than 4:1, less than 3.5:1, less than 3.25:1, less than 3:1, less than 2.75:1, less than 2.5:1, less than 2.4:1, less than 2.3:1, less than 2.2:1, less than 2.1:1, less than 2:1, less than 1.9:1, less than 1.8:1, less than 1.75:1, less than 1.7:1, less than 1.6:1, less than 1.5:1, less than 1.4:1, less than 1.3:1, less than 1.25:1, less than 1.2:1, less than 1.1:1, less than 1:1, less than 1:1.1, less than 1:1.2, less than 1:1.25, less than 1:1.3, less than 1:1.4, less than 1:1.5, less than 1:1.6, less than 1:1.7, less than 1:1.75, less than 1:1.8, less than 1:1.9, less than 1:2, less than 1:2.25, less than 1:2.5, less than 1:3, or less than 1:3.5).

Compositions and formulations can comprise a weight ratio of (a) clomazone or agriculturally acceptable salt thereof to (b) benzobicyclon or an agriculturally acceptable salt thereof from any of the minimum ratios described above to any of the maximum values described above. In some embodiments, the composition or formulation comprises a weight ratio of (a) clomazone or agriculturally acceptable salt thereof to (b) benzobicyclon or an agriculturally acceptable salt thereof that is sufficient to induce a synergistic herbicidal effect, and ranges from 1:4 to 50:1 (e.g., from 1:3.5 to 40:1, from 1:3.3 to 30:1, from 1:3 to 28:1, from 1:2 to 20:1, from 1:1.5 to 3.5:1, from 1:1 to 3:1, or from 1.12:1 to 2.24:1).

Formulations

The present disclosure also relates to formulations of the compositions and methods disclosed herein. In some embodiments, the formulation can be in the form of a single package formulation including both (a) penoxsulam or an agriculturally acceptable salt thereof, or clomazone or an agriculturally acceptable salt thereof, and (b) benzobicyclon or an agriculturally acceptable salt thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof, or clomazone or an agriculturally acceptable salt thereof, and/or (b) benzobicyclon or an agriculturally acceptable salt thereof is provided as an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or an agriculturally acceptable salt thereof or clomazone or an agriculturally acceptable salt thereof. In some embodiments, the additive is premixed with the benzobicyclon or agriculturally acceptable salt thereof. In some embodiments, the additive is premixed with the penoxsulam or an agriculturally acceptable salt thereof, or the clomazone or an agriculturally acceptable salt thereof and the benzobicyclon or agriculturally acceptable salt thereof.

In some embodiments, the additive is an additional pesticide. Exemplary additional pesticides include, but are not limited to, 2,4-D, acetochlor, aclonifen, amicarbazone, 4-aminopicolinic acid based herbicides, such as halauxifen, halauxifen-methyl, and those described in U.S. Pat. Nos. 7,314,849 and 7,432,227 to Balko, et al., amidosulfuron, aminocyclopyrachlor, aminopyralid, aminotriazole, ammonium thiocyanate, anilofos, asulam, azimsulfuron, atrazine, beflubutamid, benazolin, benfuresate, bensulfuron-methyl, bentazon-sodium, benzofenap, bifenox, bispyribac-sodium, bromobutide, bromacil, bromoxynil, butachlor, butafenacil, butralin, butroxydim, carbetamide, cafenstrole, carfentrazone, carfentrazone-ethyl, chlormequat, clopyralid, chlorsulfuron, chlortoluron, cinidon-ethyl, clethodim, clodinafop-propargyl, clomeprop, clomazone, cloransulam-methyl, cyanazine, cyclosulfamuron, cycloxydim, cyhalofop-butyl, daimuron, dicamba, dichlobenil, dichlorprop-P, diclofop-methyl, diclosulam, diflufenican, diflufenzopyr, dimefuron, dimethachlor, diquat, diuron, S-ethyl dipropyl-carbamothioate (EPTC), esprocarb, ethoxysulfuron, etobenzanid, fenoxaprop, fenoxaprop-ethyl, fenoxaprop-ethyl+isoxadifen-ethyl, fenoxaprop-P-ethyl, fenoxasulfone, fenquinotrione, fentrazamide, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, flurochloridone, fluroxypyr, fluroxypyr-meptyl, flurtamone, glufosinate, glufosinate-ammonium, glyphosate, halosulfuron-methyl, haloxyfop-methyl, haloxyfop-R-methyl, hexazinone, imazamethabenz, imazamox, imazapic, imazapyr, imazaquin, imazethapyr, imazosulfuron, indanofan, indaziflam, iodosulfuron, iodosulfuron-ethyl-sodium, iofensulfuron, ioxynil, ipfencarbazone, isoproturon, isoxaben, isoxaflutole, lactofen, linuron, MCPA, MCPB, mecoprop-P, mefenacet, mesosulfuron, mesosulfuron-ethyl sodium, mesotrione, metamifop, metazochlor, metazosulfuron, metosulam, metribuzin, metsulfuron, metsulfuron-methyl, molinate, MSMA, napropamide, napropamide-M, orfurazon, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, pinoxaden, pretilachlor, primisulfuron, profluazol, profoxydim, propanil, propaquizafop, propyrisulfuron, propoxycarbazone, propyzamide, prosulfocarb, prosulfuron, pyraclonil, pyraflufen-ethyl, pyrasulfotole, pyrazosulfuron-ethyl, pyrazolynate, pyribenzoxim (LGC-40863), pyributicarb, pyridate, pyriftalid, pyrimisulfan, pyroxsulam, pyroxasulfone, quinclorac, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tefuryltrione, tepraloxidim, terbacil, terbuthylazine, terbutryn, thenylchlor, thiazopyr, thifensulfuron, thifensulfuron-methyl, thiobencarb, topramezone, tralkoxydim, triafamone, triasulfuron, tribenuron, tribenuron-methyl, triafamone, triclopyr, and trifluralin, and agriculturally acceptable salts, choline salts, esters and mixtures thereof. In certain embodiments, the additional pesticide includes benzofenap, cyhalofop, daimuron, pentoxazone, esprocarb, pyrazosulfuron, butachlor, pretilachlor, metazosulfuron, bensulfuron-methyl, imazosulfuron, azimsulfuron, bromobutide, benfuresate, mesotrione, oxazichlomefone, and agriculturally acceptable salts or esters thereof, or combinations thereof. In certain embodiments, the additional pesticide includes triclopyr choline salt.

In some embodiments, the penoxsulam or an agriculturally acceptable salt thereof is provided in a premixed formulation with an additional pesticide. In some embodiments, the penoxsulam or an agriculturally acceptable salt thereof is premixed with cyhalofop-butyl, oxyfluorfen, triclopyr, or combinations thereof. Exemplary premixes of penoxsulam or an agriculturally acceptable salt or ester thereof and an additive that are or have been commercially available include, but are not limited to, CLINTON® (a premix incorporating cyhalofop-butyl by Dow AgroSciences LLC), REBELEX® (a premix incorporating cyhalofop-butyl by Dow AgroSciences LLC), PINDAR GT® (a premix incorporating oxyfluorfen by Dow AgroSciences LLC), and GRASP® XTRA (a premix incorporating triclopyr by Dow AgroSciences LLC).

In some embodiments, the clomazone or an agriculturally acceptable salt thereof is provided in a premixed formulation with an additional pesticide. In some embodiments, the clomazone or an agriculturally acceptable salt or ester thereof is premixed with benzofenap, dimethachlor, ethalfluralin, metazachlor, napropamide, propanil, or combinations thereof. Exemplary premixes of clomazone or an agriculturally acceptable salt or ester thereof and an additive that are or have been commercially available include, but are not limited to, VIPER® (a premix incorporating benzofenap by Bayer CropScience), COLZOR TRIO® (a premix incorporating dimethachlor and napropamide by Syngenta), STRATEGY® (a premix incorporating ethalfluralin by Loveland Products, Inc.), NIMBUS® (a premix incorporating metazachlor by BASF Corporation), PORADO® (a premix incorporating propanil by Sharp Formulators Co., Ltd.), and RICEMAX® (a premix incorporating propanil by RiceCo, LLC).

In some embodiments, the benzobicyclon or an agriculturally acceptable salt thereof is provided in a premixed formulation with an additional pesticide.

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG (400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts and, provided they have a carboxyl group, their agriculturally acceptable derivatives thereof. In some embodiments, the safener can be cloquintocet or an ester or salt thereof, such as cloquintocet (mexyl). For example, cloquintocet can be used to antagonize harmful effects of the compositions on rice and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). The composition can be applied, for example, to the vegetation as an in-water application to a flooded rice field.

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation, or applied to soil, or applied to/into water, for example to/into flooded rice fields, to prevent the emergence or growth of vegetation by spraying (e.g., foliar spraying or spraying into the water of a flooded rice field). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, the compositions disclosed herein can be applied as dry formulations (e.g., granules, WDGs) into water.

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in rice (e.g., in direct-seeded rice, water-seeded rice, transplanted rice, or rice seedbeds prior to planting rice seeds or rice transplants).

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes-of-action. In some embodiments, the herbicidal compositions comprising a synergistic herbicidally effective amount of (a) penoxsulam or an agriculturally acceptable salt thereof, or clomazone or an agriculturally acceptable salt thereof and (b) benzobicyclon or an agriculturally acceptable salt thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions disclosed herein can be used for controlling undesirable vegetation including grasses, broadleaf weeds, sedge weeds, and combinations thereof. In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb/C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (*monochoria*, MOOKA), *Monochoria vaginalis* (Berm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

The herbicidal compositions comprising a synergistic herbicidally effective amount of (a) penoxsulam or an agriculturally acceptable salt thereof, or clomazone or an agriculturally acceptable salt thereof and (b) benzobicyclon or an agriculturally acceptable salt thereof can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In certain cases, the undesirable vegetation that can be controlled by the combination of (a) and (b) is selected from *Echinochloa oryzoides* (early watergrass, ECHOR), *Cyperus rotundus* (purple nutsedge, CYPRO), or a combination thereof.

By way of non-limiting illustration, examples of certain embodiments of the present disclosure are given below.

EXAMPLES

Evaluation of Application of Combinations of Penoxsulam and Benzobicyclon and Clomazone and Benzobicyclon for Synergistic Weed Control Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 milliliter (mL) aliquots into 16-ounce (oz.) non-perforated plastic pots with a surface area of 86.59 square centimeters ($cm^2$) leaving a headspace of 3 centimeters (cm) in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hour (h) photoperiod which was maintained at about 29° C. during the day and about 26° C. during the night. Nutrients were added as Osmocote® (17:6:10, N:P:K+minor nutrients) at 2 grams (g) per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments of penoxsulam and benzobicyclon consisted of penoxsulam and benzobicyclon, applied alone or in combination. Treatments of clomazone and benzobicyclon consisted of clomazone and benzobicyclon, applied alone or in combination. Penoxsulam was formulated as Grasp® SC, clomazone was formulated as Command® 3ME, and benzobicyclon was formulated as 3.5% flowable or as technical grade material.

Treatment requirements for each compound or herbicidal component were calculated based upon the rates being tested, the concentration of active ingredient or acid equivalent in the formulation, an application volume of 2 mL per component per pot, and an application area of 86.59 $cm^2$ per pot.

For formulated compounds, a measured amount was placed in an individual 100 or 200 mL glass vial and was dissolved in a volume of 1.25% volume per volume (v/v) Agri-Dex® crop oil concentrate to obtain application solutions. If the test compound did not dissolve readily, the mixture was warmed and/or sonicated.

For technical grade compounds, a weighed amount can be placed in an individual 100 to 200 mL glass vial and dissolved in a volume of acetone to obtain concentrated stock solutions. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

The treated plots and control plots were rated blindly for visual injury of the undesirable vegetation at 22 days after application. Ratings were based on a scale of 0-100%, as discussed above, wherein 0% indicates no injury to the undesired vegetation and 100% indicates complete control of the undesired vegetation.

Colby's equation was used to determine the herbicidal effects expected from the mixtures, as described above. The results measured at 22 days following application of the compositions are provided in Table 1 (Penoxsulam and Benzobicyclon) and Table 2 (Clomazone and Benzobicyclon).

The trials exhibited unexpected synergy, and those results were found statistically significant under the p-value test. The herbicide tank mix combinations tested, application rates and ratios employed, plant species tested, and results are given below.

TABLE 1

Synergistic Weed Control Activity of In-Water Application of Penoxsulam and Benzobicyclon Alone and in Combination in Transplanted Rice in the Greenhouse.

| Penoxsulam | Benzobicyclon | % Visual Weed Control 22DAA† ECHOR | |
|---|---|---|---|
| g ai/ha | g ai/ha | Observed | Colby predicted |
| 10 | 0 | 85 | — |
| 0 | 25 | 0 | — |
| 0 | 50 | 10 | — |
| 0 | 100 | 15 | — |
| 10 | 25 | 100 | 85 |
| 10 | 50 | 90 | 87 |
| 10 | 100 | 95 | 87 |

†Visually rated at 22 days after application = 0-100 scale, where 0 = no control and 100 = complete control;
ECHOR = Early Watergrass, *Echinochloa oryzoides*

TABLE 2

Synergistic Weed Control Activity of In-Water Applications of Clomazone and Benzobicyclon Alone and in Combination in Transplanted Rice in the Greenhouse.

| Clomazone | Benzobicyclon | % Visual Weed Control 22DAA† CYPRO | |
|---|---|---|---|
| g ai/ha | g ai/ha | Observed | Colby predicted |
| 112 | 0 | 0 | — |
| 0 | 50 | 10 | — |
| 0 | 100 | 30 | — |
| 112 | 50 | 50 | 10 |
| 112 | 100 | 90 | 30 |

†Visually rated at 22 days after application = 0-100 scale, where 0 = no control and 100 = complete control;
CYPRO = Purple Nutsedge, *Cyperus rotundus*

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising herbicides, wherein the herbicides consist of a synergistic herbicidally effective amount of (a) penoxsulam or an agriculturally acceptable salt thereof, and (b) benzobicyclon or an agriculturally acceptable salt thereof, wherein the weight ratio of (a) to (b) is from 1:15 to 1:7.

2. The composition of claim 1, wherein the weight ratio of (a) to (b) is from 1:10 to 1:7.

3. The composition of claim 1, further comprising an agriculturally acceptable adjuvant.

4. The composition of claim 3, wherein the agriculturally acceptable adjuvant includes a safener.

5. A method of controlling undesirable vegetation in rice which comprises applying to vegetation or an area adjacent the vegetation or applying to soil or water to control the emergence or growth of vegetation a herbicidal composition comprising herbicides, wherein the herbicides consist of (a) penoxsulam or an agriculturally acceptable salt thereof, and (b) benzobicyclon or an agriculturally acceptable salt thereof, wherein the weight ratio of (a) to (b) is from 1:15 to 1:7.

6. The method of claim 5, wherein (a) and (b) are applied simultaneously.

7. The method of claim 5, wherein (a) and (b) are applied into water to control the emergence of undesirable vegetation.

8. The method of claim 5, wherein (a) is applied in an amount of from 5-50 g ai/ha.

9. The method of claim 5, wherein the undesirable vegetation is controlled in water-seeded or transplanted paddy rice.

10. The method of claim 5, wherein the undesirable vegetation includes a broadleaf weed, a grass weed, a sedge weed, or a combination thereof.

11. The method of claim 5, wherein the undesirable vegetation is controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

12. The method of claim 5, wherein the undesirable vegetation comprises a herbicide resistant or tolerant weed.

13. The method of claim 5, wherein the weight ratio of (a) to (b) is from 1:10 to 1:7.

* * * * *